United States Patent [19]
Frisch et al.

[11] Patent Number: 5,763,364
[45] Date of Patent: Jun. 9, 1998

[54] THIXOTROPIC AQUEOUS PLANT PROTECTION AGENT SUSPENSIONS

[75] Inventors: Gerhard Frisch, Wehrheim; Thomas Maier, Hofheim, both of Germany

[73] Assignee: Hoechst Schering AgrEvo GmbH, Berlin, Germany

[21] Appl. No.: 531,166

[22] Filed: Sep. 19, 1995

[30] Foreign Application Priority Data

Sep. 21, 1994 [DE] Germany ............ 44 33 653.5

[51] Int. Cl.$^6$ .................... A01N 25/08; A01N 43/24; A01N 47/10; A01N 47/28
[52] U.S. Cl. .................... 504/116; 504/210; 504/227; 504/301; 504/327; 504/350; 514/237.5; 514/398; 514/417; 514/431; 514/478; 514/483; 514/493; 514/525; 514/711; 514/770
[58] Field of Search ............ 504/116, 210, 504/227, 307, 327, 350; 514/770, 237.5, 398, 417, 431, 478, 483, 493, 525, 711; 71/DIG. 1

[56] References Cited

U.S. PATENT DOCUMENTS

| | | | |
|---|---|---|---|
| 4,266,965 | 5/1981 | Simons | 71/118 |
| 4,804,399 | 2/1989 | Albrecht et al. | 71/93 |
| 5,341,932 | 8/1994 | Chen et al. | 206/524.7 |
| 5,376,621 | 12/1994 | Frisch et al. | 504/330 |

FOREIGN PATENT DOCUMENTS

| | | |
|---|---|---|
| 1239804 | 8/1988 | Canada. |
| 2068824 | 11/1988 | Canada. |
| 022925 | 1/1981 | European Pat. Off.. |
| 0028052 | 5/1981 | European Pat. Off.. |
| 0110174 | 6/1984 | European Pat. Off.. |
| 0425729 | 5/1991 | European Pat. Off.. |

OTHER PUBLICATIONS

Chemical Patents Index. Documentation Abstracts Journal, Week 9343, Jan. 5, 1994, Abstract No. 93–339958.
Chemical Patents Index. Documentation Abstracts Journal, Week 9348, Feb. 9, 1994, Abstract No. 93–382964.
Othmer et al., 1978, Encyclopedia Chemical Technology, Third Edition, vol. 6, Wiley & Sons, NY, pp. 190–206 entitled "Clays".

*Primary Examiner*—S. Mark Clardy
*Attorney, Agent, or Firm*—Frommer Lawrence & Haug LLP

[57] ABSTRACT

The invention relates to thixotropic aqueous suspension concentrates of plant protection agents. The invention furthermore relates to the use of these agents in plant protection and the use of saponites as auxiliaries in the preparation of plant protection agent suspensions by wet grinding of the solid constituents.

9 Claims, No Drawings

THIXOTROPIC AQUEOUS PLANT PROTECTION AGENT SUSPENSIONS

RELATED APPLICATIONS

This application claims priority to German Application No. P 44 33 653.5, filed Sep. 21, 1994, incorporated herein by reference.

Several publications are referenced in this application. These references describe the state of the art to which this invention pertains, and are incorporated herein by reference.

BACKGROUND OF THE INVENTION

The invention relates to thixotropic aqueous suspension concentrates of plant protection agents which comprise a saponite.

As is known, solid plant protection active compounds can be formulated in the form of aqueous suspensions. It is advantageous, but not essential, if the corresponding active compounds have a melting point above 70° C. and a water-solubility at room temperature of $\leq 100$ ppm. The preparation is carried out in a known form, for example by wet grinding a mixture of water, surfactants, active compounds and further auxiliaries, for example in a ball mill. Finely ground suspensions of low to moderate viscosity, the particle size of which is usually in the particle range of $\leq 10$ μm for 90% of all the particles, are obtained in this manner. To prevent, above all, sedimentation of the dispersed particles, which as a rule have a density which is greater than that of the carrier phase (including the dissolved contents), thickeners of an organic and/or inorganic nature can be added in order to increase the viscosity of the liquid phase and thus to reduce sedimentation of the finely ground particles (EP-A-134 462). Slightly thixotropic properties of the aqueous suspension would be ideal.

The space/time ratio during the wet grinding is of great importance in the preparation of aqueous dispersions of solids. For various reasons, it is of interest to be able to process a large quantity in the shortest possible time without any loss in quality, i.e. in particular to achieve a uniform particle distribution without an additional heat effect, without crystal growth and without agglomeration.

Surprisingly, it has now been found that known aqueous plant protection agent suspensions, such as, for example, suspensions of linuron, carbendazim and isoproturon and the like (cf. EP-A-110 174, EP-A-514 768, EP-A-592 880), can be rendered thixotropic by addition of a saponite of a synthetic and/or naturally occurring type such that in the resting state of the aqueous suspension the sedimentation properties tend toward zero, but with gentle agitation or vibration, this suspension liquefies readily and is readily free-flowing.

It is furthermore surprising that the grinding times can be reduced drastically by the addition of saponite and that the suspension concentrate obtained in such a gentle manner has the desired physico-chemical data and therefore meets the quality requirements expected of suspension concentrates. Subsequent incorporation of the inorganic and/or organic thickening agents used to date can therefore be omitted.

DESCRIPTION OF THE INVENTION

The invention relates to liquid plant protection agents in the form of aqueous suspension concentrates which comprise a saponite, in addition to the active compound or active compound mixture.

The suspension concentrate preferably comprises 1–70% by weight, in particular 5 to 50% by weight, of an active compound or active compound mixture, which are preferably chosen from the group consisting of insecticides, attractants, sterilizing agents, acaricides, nematicides, fungicides, growth-regulating substances or herbicides. It is occasionally advantageous if the active compound or the active compound mixture has a melting point of above 70° C. and a low water-solubility, preferably a water-solubility of $\leq 100$ ppm at room temperature.

Possible active compounds for the compositions according to the invention are, for example, insecticides, such as endosulfan or deltamethrin, fungicides, such as captafol, captan, dimethomorph, chlorthalonil, propamocarb, pyrimethanil, triphenyltin compounds, in particular fentin hydroxide, and carbendazim, maneb or mancozeb or herbicides, such as, for example, of the urea derivative type, such as amidosulfuron, diuron, linuron, monolinuron, monuron, isoproturon and chlorotoluron, in particular amidosulfuron, diuron and chlorotoluron, or mixtures thereof, or triazine derivatives, such as simazine, cyanazine, atrazine or metamitron or biscarbamates, such as phenmedipham or desmedipham, or methanesulfonates, such as ethofumesate.

The content of saponite is preferably 0.01–6% by weight, in particular 0.1–3% by weight. Saponites are swellable monoclinic clay minerals which belong to the trioctahedral smectites. The saponites of a synthetic or naturally occurring nature in question according to the invention are magnesium aluminum silicates of the formula

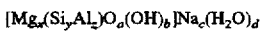

where: x=2–4, preferably 3; y=2–4, preferably 3; z=0.1–1 preferably, 0.2–0.4; a=8–12 preferably, 10; b=1–5, preferably 1–3; c=0.1–0.6 preferably, 0.2–0.4; and d=1–8 preferably, 1–2.

In these laminar silicates, some of the tetravalent Si ions are replaced by trivalent Al ions. The resulting negative excess charge in the silicate layers is compensated by intermediate Na ions. Other suitable cations can also be incorporated instead of $Na^+$. Saponite SKS 20 (Hoechst Aktiengesellschaft) is preferred.

The thixotropic suspension concentrates according to the invention as a rule comprise 0.1–25% by weight, preferably 0.5–15% by weight, of customary auxiliaries, which are preferably chosen from the series consisting of wetting and dispersing agents, defoamers, thickeners, preservatives and antifreezes.

Possible additional wetting and dispersing agents are, for example, ®Darvan No. 3, ®Vanisperse CB, ®Luviskol K 30, Reserve C, ®Forlanit P, ®Sokalan CP10, ®Maranil A, ®Genapol PF40, ®Genapol LRO, tributylphenol polyglycol ethers, such as the ®Sapogenat T brands (Hoechst), nonylphenol polyglycol ethers, such as the ®Arkopal N brands (Hoechst) or tristyrylphenol polyglycol ether derivatives.

Suitable defoamers are, for example, those based on silicone, such as those from the ®Silcolapse series (Rhone Poulenc) or the antifoam series from Wacker.

Thickeners can be inorganic or organic in nature; they can also be combined. Suitable thickeners are, for example, those based on aluminum silicate, xanthan, methylcellulose, polysaccharide, alkaline earth metal silicate, gelatin and polyvinyl alcohol, such as, for example, ®Bentone EW, ®Veegum, ®Rhodopol 23 or ®Kelzan S.

If necessary, preservatives, for example those based on formaldehyde, benzoic acid and triphenyltin, are used.

Antifreezes, such as urea, salts, polyols (for example glycol, propylene glycol or glycerol) or sugars, can also be added.

To prepare the suspension concentrates according to the invention, the components are stirred with water, the resulting coarse-particle suspension is pre-comminuted, if appropriate, by grinding in a corundum or toothed disk mill down to finenesses of about 200 µm, and the product is then ground for example in ball mills or sand mills, until the particles of the dispersion are present in particle sizes of 0.01 to 10 µm, preferably under 5 µm. The particle sizes can be determined by means of a disk centrifuge or by laser diffraction.

The invention therefore also relates to the use of saponites as auxiliaries in the preparation of plant protection agent suspensions by wet grinding of the solid constituents.

The suspension concentrates according to the invention are used in plant protection in a simple manner by diluting the concentrates with the desired amount of water, if appropriate, to form a spray liquid, briefly stirring this and applying it in an active amount on to the harmful insects, Acarina, nematodes, harmful fungi or harmful plants or the areas or substrates affected by these or to seed or plants.

EXAMPLES

The invention is further illustrated by the following examples, which are intended neither to define nor limit the invention in any manner.

The thixotropic suspension concentrates according to the invention were obtained starting from the following commercially conventional recipes by adding saponite and grinding in a Netzsch mill. Details of the composition and the physical properties of the concentrates can be seen in Table 1.

| Composition 1: | |
|---|---|
| 39.0% | of limuron active ingredient |
| 10.0% | of glycerol (99% pure) |
| 2.0% | of silicone defoamer |
| 1.0% | of ®Darvan No. 3 |
| 0.1% | of preservative |
| 3.0% | of ligninsulfonate CS |
| 0.5% | of tributylphenol |
| 0.5% | of ®Luviskol K30 |
| to 100% | water |
| Composition 2: | |
| 23.02% | of isoproturon active ingredient |
| 5.64% | of ioxynil active ingredient |
| 15.98% | of mecoprop-P DMA salt active ingredient |
| 4.00% | of ®Reserve C |
| 2.00% | of ®Forlanit P |
| 1.00% | of silicone defoamer |
| 0.10% | of preservative |
| to 100% | water |
| Composition 3: | |
| 46.5% | of isoproturon active ingredient |
| 6.0% | of ®Reserve C |
| 3.0% | of ®Forlanit P |
| 1.0% | of silicone defoamer |
| 10.0% | of glycol |
| to 100% | water |
| Composition 4: | |
| 39.78% | of isoproturon active ingredient |
| 1.52% | of amidosulfuron active ingredient |
| 10.00% | of ®Sokalan CP10 |
| 8.00% | of glycerol |
| 7.00% | of ®Maranil A |
| 1.00% | of ®Darvan No. 3 |
| 1.00% | of silicone defoamer |
| 0.10% | of preservative |
| to 100% | water |
| Composition 5: | |
| 31.90% | of carbendazim active ingredient |
| 7.50% | of glycol |
| 2.25% | of silicone defoamer |
| 3.00% | of ligninsulfonate CB |
| 2.25% | of ®Genapol PF 40 |
| 0.75% | of ®Genapol LRO |
| to 100% | water |
| Composition 6: | |
| 41.75% | of carbendazim active ingredient |
| 8.00% | of glycol |
| 3.00% | of silicone defoamer |
| 4.00% | of ligninsulfonate CB |
| 3.00% | of ®Genapol PF 40 |
| 1.00% | of ®Genapol LRO |
| to 100% | water |

Notes regarding the Examples:

The silicone-based defoamer is the commercial product ®Silicolapse 5020 from Rhone Poulenc;

The preservative is a commercial product from Riedel-de Haen;

®Darvan No. 3 from R. T. Vanderbuilt Comp. Norwalk, Conn. 06855, USA—data sheet 07.01.81 is a product based on an Na salt of polymerized substituted alkylbenzenesulfonic acids;

®Vanispersee CB from Borregaard Industries Ltd., Sarpsborg, Norway is a ligninsulfonate with 0.17 sulfonic acid group per phenylpropane unit, a total sulfur content of 2.4% and a pH of 8.8 (3% strength solution);

®Luviskol K30 is a polyacrylate from BASF, Ludwigshafen.

®Sokalan CP10 is a modified Na polyacrylate of low molecular weight which is prepared by a special polymerization process. (BASF Technical Information sheet TI/P 3039 d of 1988.)

®Maranil is a dodecylbenzenesulfonate Na salt from Henkel.

®Genapol LRO (Hoechst AG) is an alkyl polyglycol ether sulfate.

®Genapol PF400 (Hoechst AG) is a polyethylenepolypropylene block copolymer.

®Reserve C (Hoechst AG) is a condensation product of phenols, cresols, formaldehyde and alkali metal sulfite.

TABLE I

| Product | Grinding time | Grinding Time reduction | Addition of % of saponite SKS 20 | Thixotropic character | Flow properties | Evaluation | Comments |
|---|---|---|---|---|---|---|---|
| Composition 6 | 1 h | 1 h | 0.75 | yes | good | stable | |
| Composition 6 | 1 h | 1 h | 0.50 | yes | good | stable | |
| Composition 6 | 1 h | 1 h | 1.00 | yes | good | stable | |

TABLE I-continued

| Product | Grinding time | Grinding Time reduction | Addition of % of saponite SKS 20 | Thixotropic character | Flow properties | Evaluation | Comments |
|---|---|---|---|---|---|---|---|
| Composition 6 | 1 h | 1 h | 1.50 | yes | good | stable | |
| Composition 6 | 1 h | 1 h | 0.80 | yes | good | stable | |
| Composition 6 | 1 h | 1 h | 0.90 | yes | good | stable | |
| Composition 5 | 1 h | 1 h | 0.50 | no | good | stable | |
| Composition 5 | 1 h | 1 h | 0.75 | yes | good | stable | |
| Composition 5 | 1 h | 1 h | 1.00 | yes | good | stable | |
| Composition 5 | 1 h | 1 h | 1.50 | yes | good | stable | |
| Composition 5 | 1 h | 1 h | 0.80 | yes | good | stable | |
| Composition 5 | 1 h | 1 h | 0.90 | yes | good | stable | |
| Composition 4 | 1 h | / | 0.50 | yes | highly viscous | stable | foamy |
| Composition 4 | 3 h | / | 0.75 | yes | highly viscous | stable | foamy |
| Composition 2 | 2 h | / | 0.75 | yes | good | stable | |
| Composition 3 | 2 h | / | 0.50 | yes | good | stable | |
| Composition 3 | 2 h | / | 0.75 | yes | good | stable | |
| Composition 1 | 2 h | 1 h | 0.50 | yes | good | stable | |

Grinding was carried out in a Netzsch mill at 1000 rpm.
The ratio of the beads to the product was 2:1
All the Compositions listed in the table are chemically and physically stable at between −10° C. and +50° C. for at least 3 months.

We claim:

1. A liquid plant protection agent in the form of a thixotropic aqueous suspension concentrate, which comprises 1–70% by weight of at least one active compound selected from the group consisting of endosulfan, propamocarb, pyrimethanil, captafol, captan, dimethomorph, chlorthalonil, triphenyltin compounds, carbendazim, maneb, mancozeb, herbicides of the urea derivative type, triazine derivatives, biscarbamates and methanesulfonates; and 0.01–3% by weight of a saponite, wherein the particles of said suspension are present in particle sizes 0.01 to 10 μm.

2. An agent as claimed in claim 1, which comprises 5 to 50% by weight of active compound or active compound mixture and 0.1 to 3% by weight of saponite.

3. An agent as claimed in claim 1, comprising 0.1 to 25% by weight of customary auxiliaries from the series consisting of wetting and dispersing agents, defoamers, thickeners, preservatives and antifreezes.

4. A method of reducing the grinding time of a process for the preparation of a plant protection agent suspension, comprising the step of adding a saponite to the suspension prior to wet-milling.

5. The process according to claim 4, wherein the plant protection agent suspension is in the form of a thixotropic aqueous suspension concentrate which comprises 1–70% by weight of at least one active compound selected from the group consisting of endosulfan, propamocarb, pyrimethanil, captafol, captan, dimethomorph, chlorthalonil, triphenyltin compounds, carbendazim, maneb, mancozeb, herbicides of the urea derivative type, triazine derivatives, biscarbamates and methanesulfonates; and 0.01–3% by weight of a saponite, wherein the particles of said suspension are present in particle sizes 0.01 to 10 μm.

6. The process according to claim 4, wherein the plant protection agent comprises 5 to 50% by weight of active compound or active compound mixture and 0.1 to 3% by weight of saponite.

7. The process according to claim 4, wherein the plant protection agent comprises 0.1 to 25% by weight of customary auxiliaries selected from the group consisting of wetting and dispersing agents, defoamers, thickness, preservatives and antifreezes.

8. A method of combating harmful insects, Acarina, nematodes, harmful fungi or harmful plants, which comprises applying from an aqueous dilution an active amount of an agent as claimed in claim 1 to these organisms or the areas or substrates affected by them or to seed or plants.

9. A method of combatting harmful insects, Acarina, nematodes, harmful fungi or harmful plants, which comprises applying to said organism or to areas or substrates affected by then or to seed or plants an effective amount of a plant protection agent suspension wherein said suspension is produced by the method of claim 4.

* * * * *